US012426977B2

(12) United States Patent
Hares

(10) Patent No.: US 12,426,977 B2
(45) Date of Patent: Sep. 30, 2025

(54) VIRTUAL CONSOLE FOR CONTROLLING A SURGICAL ROBOT

(71) Applicant: CMR Surgical Limited, Cambridge (GB)

(72) Inventor: Luke David Ronald Hares, Cambridge (GB)

(73) Assignee: CMR Surgical Limited, Cambridge (GB)

( * ) Notice: Subject to any disclaimer, the term of this patent is extended or adjusted under 35 U.S.C. 154(b) by 491 days.

(21) Appl. No.: 17/907,133

(22) PCT Filed: Mar. 23, 2021

(86) PCT No.: PCT/GB2021/050708
§ 371 (c)(1),
(2) Date: Sep. 23, 2022

(87) PCT Pub. No.: WO2021/191598
PCT Pub. Date: Sep. 30, 2021

(65) Prior Publication Data
US 2023/0329818 A1    Oct. 19, 2023

(30) Foreign Application Priority Data
Mar. 23, 2020    (GB) ...................................... 2004206

(51) Int. Cl.
*A61B 34/00*    (2016.01)
*A61B 34/20*    (2016.01)
(Continued)

(52) U.S. Cl.
CPC .............. *A61B 34/74* (2016.02); *A61B 34/20* (2016.02); *A61B 34/25* (2016.02); *A61B 34/35* (2016.02); *A61B 34/37* (2016.02)

(58) Field of Classification Search
CPC ................................ A61B 34/74; A61B 34/35
See application file for complete search history.

(56) References Cited

U.S. PATENT DOCUMENTS

2009/0192524 A1 *    7/2009    Itkowitz ................. B25J 9/1689
                                                        606/130
2011/0238079 A1      9/2011    Hannaford
(Continued)

FOREIGN PATENT DOCUMENTS

EP         3834768 A1      6/2021
JP       2017-514608 A2    6/2017
(Continued)

OTHER PUBLICATIONS

Notification of Reason for Refusal issued for JP Patent Application 2022-557858; Dispatched Date Oct. 26, 2023 (5 pages).
(Continued)

*Primary Examiner* — Carl H Layno
*Assistant Examiner* — Bryan McAllister Lee
(74) *Attorney, Agent, or Firm* — Finch & Maloney PLLC

(57) ABSTRACT

Systems and methods for controlling a surgical robot comprising a base, and an arm extending from the base to an attachment for an instrument, the arm comprising a plurality of joints whereby the configuration of the arm can be altered. The system includes: a display device configured to present a view of a virtual scene to an operator of the virtual reality display device, the virtual scene comprising a virtual screen on which a representation of a real-time video stream of a surgical site is displayed; an input tracking system configured to track a position of one or more free-space inputs in space; and a control unit configured to translate the tracked position of the one or more inputs free-space into one or more control signals to control the position of the arm of the surgical robot.

17 Claims, 8 Drawing Sheets

(51) Int. Cl.
    *A61B 34/35*        (2016.01)
    *A61B 34/37*        (2016.01)

(56)         References Cited

U.S. PATENT DOCUMENTS

2018/0078319 A1      3/2018  Nobles
2019/0005848 A1*     1/2019  Garcia Kilroy ........ G16H 40/67
2019/0380791 A1     12/2019  Fuerst

FOREIGN PATENT DOCUMENTS

JP      2019-528838  A2   10/2019
JP      2020-520521  A2    7/2020
WO        2018195319 A1   10/2015
WO        2015171614 A1   11/2015
WO        2019005983 A1    1/2019

OTHER PUBLICATIONS

International Search Report and Written Opinion PCT Application No. PCT/GB2021/050708 Date of Mailing: Jun. 14, 2021 (23 pages).
Search Report for GB Application No. GB2004206.5 Date of Mailing Aug. 26, 2020 (3 pages).
Examination Report Corresponding to GB2004206.5 mailed Apr. 2, 2024, 5 pages.

* cited by examiner

VIRTUAL CONSOLE FOR CONTROLLING A SURGICAL ROBOT

CROSS-REFERENCE TO RELATED APPLICATIONS

This application claims priority under 35 U.S.C. § 371 as a national stage application of PCT Application No. PCT/GB2021/050708, filed Mar. 23, 2021, which claims priority to GB 2004206.5, filed Mar. 23, 2020, each of which is hereby incorporated herein by reference in its entirety.

BACKGROUND

It is known to use robots for assisting and performing surgery. FIG. 1 illustrates a typical surgical robot 100 which consists of a base 108, an arm 102, and an instrument 105. The base supports the robot, and is itself attached rigidly to, for example, the operating theatre floor, the operating theatre ceiling or a trolley. The arm extends between the base and the instrument. The arm is articulated by means of multiple flexible joints 103 along its length, which are used to locate the surgical instrument in a desired location relative to the patient. The surgical instrument is attached to the distal end 104 of the robot arm. The surgical instrument penetrates the body of the patient 101 at a port 107 so as to access the surgical site. At its distal end, the instrument comprises an end effector 106 for engaging in a medical procedure. Although the surgical robot 100 of FIG. 1 has a single arm, in other examples a surgical robot may comprise multiple arms, each capable of being coupled to a different instrument; or there may be multiple surgical robots each capable of being coupled to one or more instruments.

A surgical robot 100 is typically controlled remotely by an operator (e.g. surgeon) via a physical operator console that may be located in the same room (e.g. operating theatre) as the surgical robot 100 or remotely from it. An example physical operator console 200 is shown in FIG. 2. The operator console 200 comprises input devices 202, 204 for controlling the state of the arm 102 and/or instrument 105 attached thereto. The input devices 202, 204 may be, for example, handgrips or hand controllers (e.g. one for each hand), with one or more buttons thereon, mounted on parallelogram linkages. A control system converts the movement of the hand controllers into control signals to move the arm joints and/or instrument end effector of the surgical robot. In some cases, the control system is configured to generate control signals to move the arm joints and/or instrument end effector based on the position in space of the hand controllers and their orientation. The operator console 200 also comprises a display 206. The display 206 is arranged to be visible to an operator (e.g. surgeon) operating the input devices 202, 204. The display is used to display a video stream of the surgical site (e.g. a video stream captured by an endoscope, and/or a video stream captured another camera or microscope (such as those used in open surgery)) and/or other information to aid the operator (e.g. surgeon) in performing the surgery. The display may be two-dimensional (2D) or three-dimensional (3D).

While the physical operator console may be situated remotely from the surgical robot it is preferable to have the physical operator console in the same room (e.g. operating theatre) as the surgical robot, where possible, to allow the operator (e.g. surgeon) to be in the same room as (and thus in close proximity to) the patient and the rest of the surgical team. Generally, the surgical robot or surgical robots are placed around the bed of the patient in the central part of the operating theatre with the physical operator console located elsewhere, typically toward the periphery of the room. While physical operator consoles for controlling a surgical robot allow an operator (e.g. surgeon) very precise control of a surgical robot, they are often quite large and bulky, thus take up a lot of space. Often their size limits the configuration and set-up of the operating theatre as there may only be one or two configurations of the operating theatre that accommodate the physical operator console and all of the other required equipment such as, but not limited to, the anaesthesia cart. Their size may also make it difficult to move the console within a hospital or surgery (e.g. between different operating rooms) or to the hospital or surgery in the first place Such physical operator consoles are also typically quite expensive which may pose an impediment to a hospital or surgery from implementing a surgical robotic system.

Accordingly, there is a desire for a small (e.g. in terms of footprint) and inexpensive means or system for accurately controlling a surgical robot.

The embodiments described below are provided by way of example only and are not limiting of implementations which solve any or all of the disadvantages of known surgical robot systems and/or control systems therefor.

SUMMARY

This summary is provided to introduce a selection of concepts that are further described below in the detailed description. This summary is not intended to identify key features or essential features of the claimed subject matter, nor is it intended to be used to limit the scope of the claimed subject matter.

Described herein are systems and methods for controlling a surgical robot comprising a base, and an arm extending from the base to an attachment for an instrument, the arm comprising a plurality of joints whereby the configuration of the arm can be altered. The system includes: a virtual reality display device configured to present a view of a virtual reality scene to an operator of the virtual reality display device, the virtual reality scene comprising a virtual screen on which a representation of a real-time video stream of a surgical site is displayed; an input tracking system configured to track a position and/or orientation of one or more free-space inputs in space; and a control unit configured to translate the tracked position and/or orientation of the one or more free-space inputs into one or more control signals to control the position of the arm of the surgical robot.

A first aspect provides a system for controlling a surgical robot, the surgical robot comprising a base, and an arm extending from the base to an attachment for an instrument, the arm comprising a plurality of joints whereby the configuration of the arm can be altered, the system comprising: a display device configured to present a virtual screen to an operator of the display device, wherein a representation of a real-time video stream of a surgical site is displayed on the virtual screen; an input tracking system configured to track a position and/or orientation of one or more free-space inputs; and a control unit configured to translate the tracked position and/or orientation of the one or more free-space inputs into one or more control signals which control the position of the arm of the surgical robot.

The display device may comprise a virtual reality display device configured to present a view of a virtual reality scene to the operator of the virtual reality display device, the virtual reality scene comprising the virtual screen.

The virtual reality display device may comprise a virtual reality headset.

The virtual reality display device may comprise one or more sensors configured to track a position of the operator's head and/or the operator's gaze when the operator is using the virtual reality display device, and the virtual reality display device may be further configured to present a different view of the virtual reality scene to the operator in response to detecting from the one or more sensors a change in position of the operator's head and/or a change in the operator's gaze.

The virtual reality display device may be configured to, in response to detecting that operator's head and/or the operator's gaze is in a first position, presenting a view of the virtual reality scene in which the virtual screen is visible.

The virtual reality display device may be configured to, in response to detecting that the operator's head and/or the operator's gaze has moved in a first direction with respect to the first position, presenting a view of the virtual reality scene in which another virtual object is displayed.

The other virtual object may be a real-time representation of the surgical robot.

The other virtual object may be a real-time representation of the surgical robot and a patient.

The other virtual object may be a representation of one or more patient pre-operative scans.

The virtual reality display device may be configured to, in response to detecting that the operator's head and/or the operator's gaze has moved in a second direction with respect to the first position, present a view of the virtual reality scene in which a further virtual object is displayed.

The display device may comprise an augmented reality display device or a mixed reality display device configured to present the virtual screen to the operator as a virtual object in the real world.

The display device may comprise an augmented reality headset or a mixed reality headset.

The display device may comprise one or more sensors configured to track a position of the operator's head and/or the operator's gaze when the operator is using the display device, and the display device may be further configured to present a different view of the virtual screen to the operator in response to detecting from the one or more sensors a change in position of the operator's head and/or a change in the operator's gaze.

The field of view of the surgical site shown in the video stream may not be automatically controlled by movement of the operator's head or the operator's gaze.

The one or more free-space inputs may comprise a hand controller.

The control unit may be further configured to cause force feedback to be provided to the operator in response to detecting that the arm of the surgical robot or the instrument attached thereto has had force exerted thereon.

The control unit may be further configured to adjust a parameter of the force feedback based on a magnitude of the detected force.

The video stream of the surgical site may be captured by an endoscope.

The endoscope may be attached to an arm of the surgical robot and the position of the endoscope may be controlled by the surgical robot.

The display device may be further configured to receive the video stream of the surgical site and generate the virtual screen from the video stream of the surgical site.

The system may further comprise the surgical robot.

The real-time video stream of the surgical site may be captured by an image capture device. The control unit may be further configured to receive operator input from at least one of the one or more free form inputs indicating a desired position and/or field of view of the image capture device and control the position and/or field of view of the image capture device in dependence on the received operator input.

A second aspect provides a method of controlling a surgical robot, the surgical robot comprising a base, and an arm extending from the base to an attachment for an instrument, the arm comprising a plurality of joints whereby the configuration of the arm can be altered, the method comprising: presenting, using a display device, a virtual screen on which a representation of a video stream of a surgical site is displayed; tracking, using an input tracking system, the position in space of one or more free-space inputs; and translating the tracked position of the one or more inputs into one or more control signals to control the position of the arm of the surgical robot.

The method may further comprise receiving the video stream of the surgical site; and generating the virtual screen from the video stream of the surgical site.

The above features may be combined as appropriate, as would be apparent to a skilled person, and may be combined with any of the aspects of the examples described herein.

BRIEF DESCRIPTION OF THE DRAWINGS

Examples will now be described in detail with reference to the accompanying drawings in which.

Figure 1:
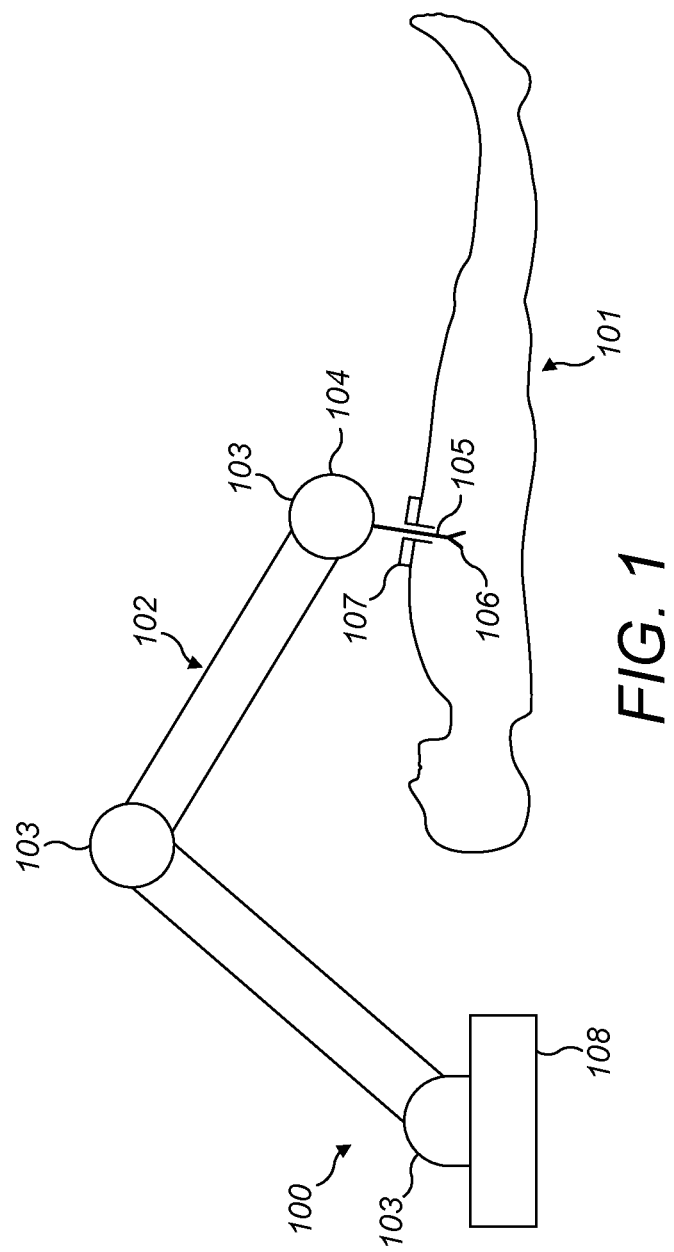
FIG. 1 is a schematic diagram of an example surgical robot performing an example surgical procedure.

The accompanying drawings illustrate various examples. The skilled person will appreciate that the illustrated element boundaries (e.g., boxes, groups of boxes, or other shapes) in the drawings represent one example of the boundaries. It may be that in some examples, one element may be designed as multiple elements or that multiple elements may be designed as one element. Common reference numerals are used throughout the figures, where appropriate, to indicate similar features.

DETAILED DESCRIPTION

The following description is presented by way of example to enable a person skilled in the art to make and use the invention. The present invention is not limited to the embodiments described herein and various modifications to the disclosed embodiments will be apparent to those skilled in the art. Embodiments are described by way of example only.

Described herein are systems, and methods, for controlling a surgical robot via a virtual console. Specifically, the systems comprise a virtual reality display device (such as, but not limited to, a virtual reality headset) configured to present a view of a virtual reality scene to an operator of the virtual reality display device, the virtual reality scene comprising a virtual screen on which a representation of a real-time video stream of a surgical site is displayed; an input tracking system configured to track a position and/or orientation of one or more free-space inputs in space; and a control unit configured to translate the tracked position and/or orientation of the one or more free-space inputs into one or more control signals to control the position of the arm of the surgical robot.

The systems described herein for controlling a surgical robot are typically smaller (e.g. in terms of footprint) than a physical operator console for controlling a surgical robot allowing them to be used in many more operating theatre configurations than a physical operator console. The systems described herein also provide a very natural and intuitive interface for controlling a surgical robot as they allow the operator to interact with the system (and thus control the surgical robot) in the same manner as a physical operator console. Also, as described in more detail below, by providing the operator with a virtual screen on which a representation of the video stream of the surgical site is displayed instead of providing a virtual reality scene in which the operator is immersed in the surgical site avoids the problems with mapping the operator's head movements to the video capture equipment (e.g. endoscope).

Figure 3:
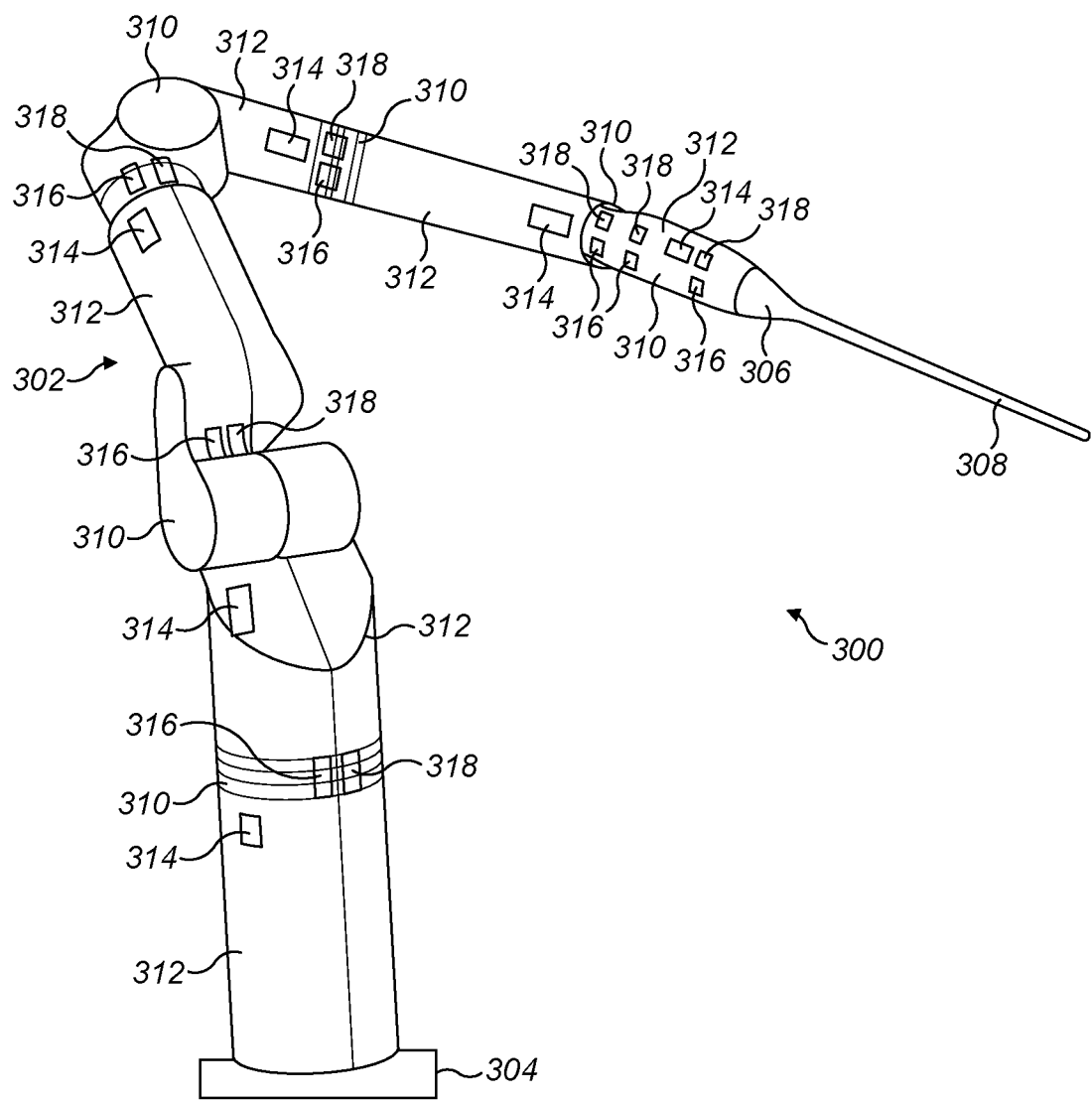
FIG. 3 is a schematic diagram of an example surgical robot.

Reference is now made to FIG. 3 which illustrates an example surgical robot 300 which may be controlled by the systems and methods described herein. The surgical robot 300 comprises an arm 302 which extends from a base 304 which is fixed in place when a surgical procedure is being performed. In some cases, the base 304 may be mounted to a chassis. The chassis may be a cart, for example a bedside cart for mounting the robot at bed height. Alternatively, the chassis may be a ceiling mounted device, or a bed mounted device.

The arm 302 extends from the base 304 of the robot to an attachment 306 for a surgical instrument 308. The arm is flexible. It is articulated by means of multiple flexible joints 310 along its length. In between the joints are rigid arm members 312. The arm in FIG. 3 has seven joints. The joints include one or more roll joints (which have an axis of rotation along the longitudinal direction of the arm members on either side of the joint), one or more pitch joints (which have an axis of rotation transverse to the longitudinal direction of the preceding arm member), and one or more yaw joints (which also have an axis of rotation transverse to the longitudinal direction of the preceding arm member and also transverse to the rotation axis of a co-located pitch joint). However, the arm could be jointed differently. For example, the arm may have fewer or more joints. The arm may include joints that permit motion other than rotation between respective sides of the joint, for example a telescopic joint. The robot comprises a set of drivers 314, each driver 314 drives one or more of the joints 310.

The attachment 306 enables the surgical instrument 308 to be releasably attached to the distal end of the arm. The surgical instrument 308 has a linear rigid shaft and a working tip at the distal end of the shaft. The working tip comprises an end effector for engaging in a medical procedure. The surgical instrument may be configured to extend linearly parallel with the rotation axis of the terminal joint of the arm. For example, the surgical instrument may extend along an axis coincident with the rotation axis of the terminal joint of the arm. The surgical instrument 308 could be, for example, a cutting device, a grasping device, a cauterising device or image capture device (e.g. endoscope).

The robot arm comprises a series of sensors 316, 318. These sensors comprise, for each joint, a position sensor 316 for sensing the position of the joint, and a torque sensor 318 for sensing the applied torque about the joint's rotation axis. One or both of the position and torque sensors for a joint may be integrated with the motor for that joint.

Figure 4:
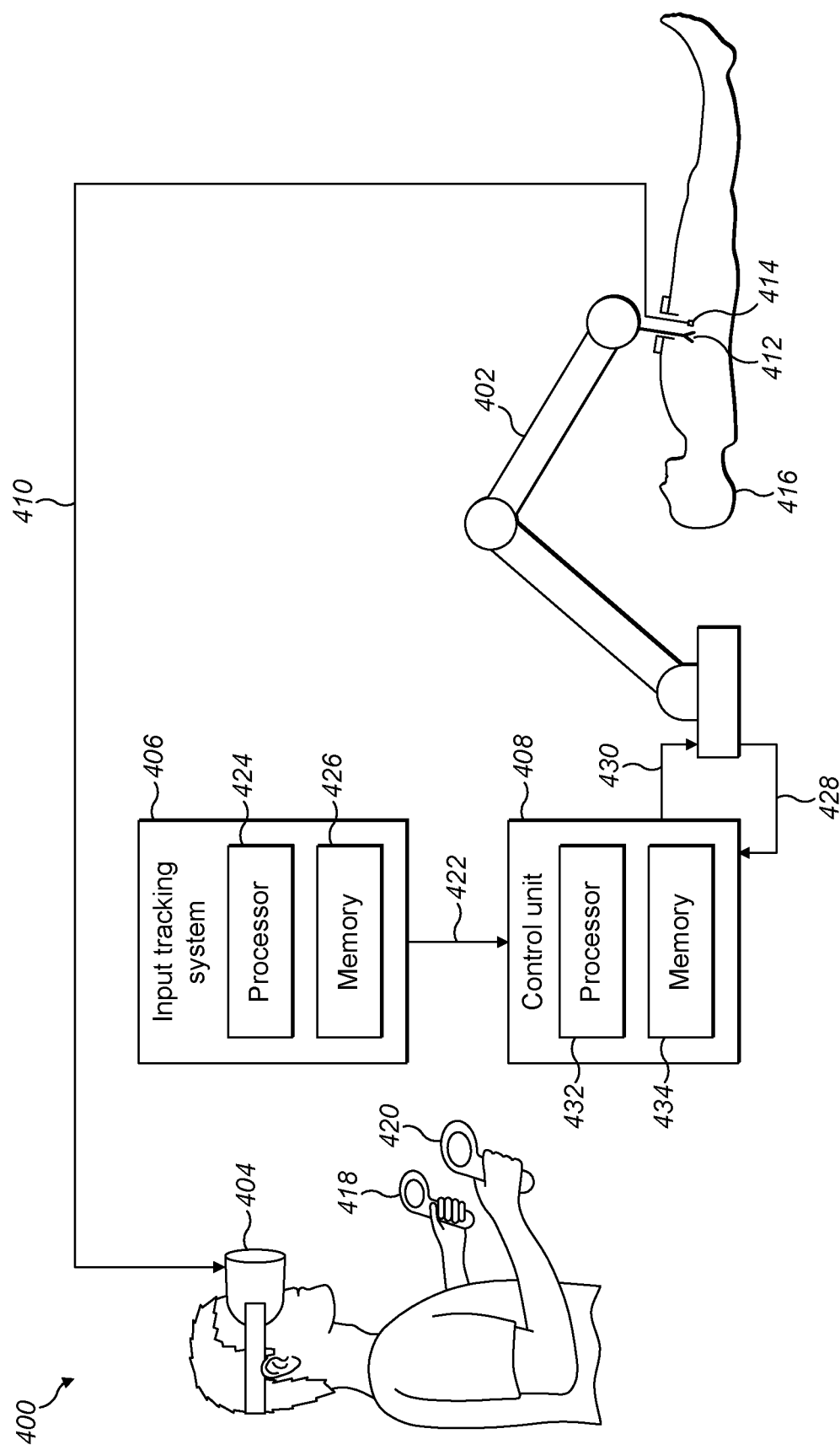
FIG. 4 is a block diagram of an example system for controlling a surgical robot.

Reference is now made to FIG. 4 which illustrates an example system 400 for controlling the operation of a surgical robot 402 (which may be implemented as the surgical robot 300 of FIG. 3) via a virtual console.

The system 400 comprises a virtual reality display device 404, an input tracking system 406 and a control unit 408.

The virtual reality display device 404 is configured to receive a video stream 410 of the surgical site 412; generate a virtual reality scene comprising a virtual screen on which a real-time representation of the video stream is displayed; and present a view of the virtual reality scene to the operator of the virtual reality display device. The video stream 410 of the surgical site 412 may be captured by an endoscope 414 or another suitable image capture device. As is known to those of skill in the art, during a surgical procedure performed by a robot, an endoscope 414 is typically inserted through a small incision or natural opening in the body, such as, but not limited to, the mouth or nostrils. An endoscope is a rigid or flexible tube that comprises a set of optical fibres that provide light to a surgical site and capture the reflected light. The reflected light represents real-time images (i.e. video stream) of the surgical site. In some cases, the endoscope itself may comprise a tiny camera at its tip that converts the reflected light into real-time images. However, in other cases, the reflected light captured by the endoscope tip is provided to a larger camera which converts the reflected light into real-time images. The operator (e.g. surgeon) of the surgical robot uses the real-time images of the surgical site to determine what surgical steps are to be performed and controls the surgical robot to perform the desired surgical steps. The video stream 410 of the surgical site 412 may be provided to the virtual reality display device 404 from the image capture device (e.g. endoscope 414) in any suitable manner. For example, the video stream of the surgical site may be provided, directly or indirectly, from the image capture device (e.g. endoscope 414) to the virtual reality display device 404 via a wired or wireless communication connection such as, but not limited to, an Ethernet or Wi-Fi® connection.

In some cases, the video stream 410 of the surgical site 412 may be captured by an image capture device 415 (e.g. endoscope) attached to, and controlled by, one of the robot arms of the surgical robot 402. However, in other cases, the video stream 410 of the surgical site 412 may be captured by a manually controlled image capture device (e.g. endoscope). In some cases, where the surgical robot has multiple robot arms, the operator of the surgical robot 402 may not be able to operate a robot arm of the surgical robot 402 in surgical mode (i.e. to perform a surgical procedure) unless an operative endoscope is attached to, and controlled by, one of the robot arms.

In contrast to known virtual reality display devices for use in performing surgery, such as that described in US Published Patent Application No. 2017/0181802, the virtual reality display device 404 of FIG. 4 does not generate a virtual reality scene (based on the video stream) that makes the operator (e.g. surgeon) feel as they are immersed within the body of the patient 416. Specifically, known virtual reality display devices for use in performing surgery receive a video stream of the surgical site and generate a virtual reality scene therefrom that makes the operator feel as if they are within the patient's body. In many of these systems, to make the immersive experience complete, the position of the operator's head is tracked and when the operator moves their head, the field of view of the image capture device (e.g. endoscope) is automatically adjusted in accordance with the operator's head so as to present the operator with a different virtual view of the surgical site. For example, if the operator moves their head to the right then the image capture device (e.g. endoscope) is automatically adjusted so that the field of view thereof is to the right of the previous field of view to be able to present the operator with a virtual view of the surgical site that is to the right of the previous view of the surgical site. One of the advantages of such systems is that the mapping between the position and/or movement of the input devices and the position and/or movement of the end effectors attached to the robot arm(s) does not have to change as the operator moves their head. This is because in such systems the position/movement of the input devices with respect to the operator will always match the movement of the end effectors in the virtual reality scene (e.g. once mapped, moving the input devices to the right will move the end effector to the right regardless of the field of view of the endoscope or the position of the operator's head).

However, one of the technical challenges with such systems is that an endoscope cannot typically move in the same manner as an operator's head, making it difficult to map the position and/or movement of the operator's head to the position and/or movement of the endoscope. Specifically, because an endoscope typically comprises lenses at the end of a long shaft that passes through a fulcrum at the port, the movement of the endoscope is restricted so that it cannot move in an analogous manner as the operator's head. For example, a person can turn their head roughly ninety degrees left and right, however an endoscope cannot rotate ninety degrees. This makes it difficult to map the position and/or movement of the operator's head directly to the position and/or movement of the endoscope, making it difficult to provide the operator with a truly, or complete, immersive experience.

Figure 2:
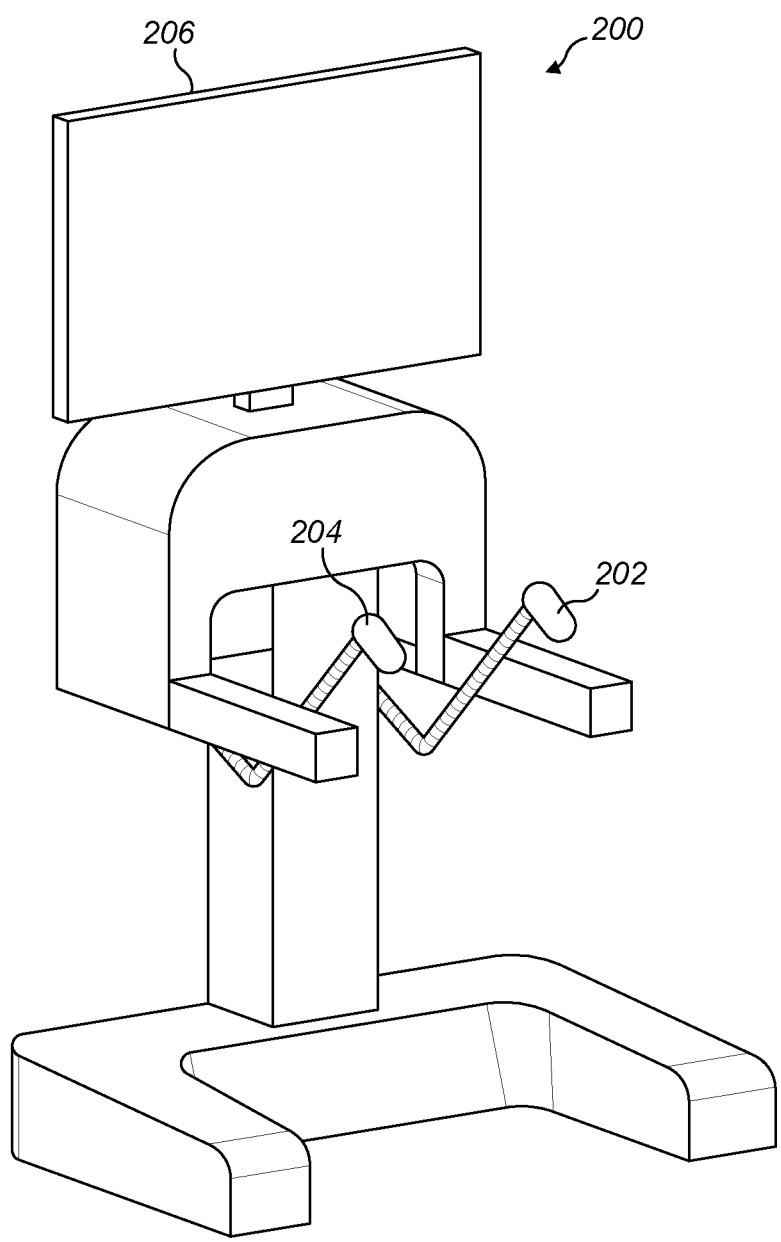
FIG. 2 is a schematic diagram of an example physical operator console.

Accordingly, in contrast to virtual reality display devices which are configured to generate a virtual reality scene that immerses the operator (e.g. surgeon) within the patient's body, in the systems and methods described herein the virtual reality display device is configured to generate a virtual reality scene comprising a virtual screen on which a representation of the video stream 410 of the surgical site 412 is displayed, much the same way that the physical display 206 in the example physical operator console 200 of FIG. 2 displays a representation of the video stream of the surgical site to the operator (e.g. surgeon). Since the representation of the video stream of the surgical site is presented on a virtual screen, movement of the operator's head may change the operator's view or perspective of the virtual screen but does not automatically change the image capture device's (e.g. endoscope's 414) field of view or perspective of the surgical site 412. Accordingly, in the systems and methods described herein the movement of the operator's head does not automatically change the image capture device's (e.g. endoscope's 414) position or field of view of the surgical site. In contrast, in the systems and methods described herein the image capture device's (e.g. endoscope's 414) position or field of view is controlled in another manner (e.g. via the one or more inputs, or manually). In this way, the operator (e.g. surgeon) can interact with the virtual screen in the same way as the operator would interact with the physical display of a physical console. This allows the system 400 described herein to provide the operator with a very intuitive control experience.

The virtual reality display device 404 may comprise a processor (not shown) configured to receive the video stream 410 of the surgical site 412; generate a virtual reality scene comprising a virtual screen on which a representation of the video stream is displayed; and present a view of the virtual reality scene to the operator. The resolution of the view of the virtual reality scene presented to the operator, and/or the latency of the real-time updates thereto may be configured such that the virtual reality scene can be used to control the surgical robot 402 to perform a surgical procedure. The virtual reality display device 404 may also comprise a sensor system to track the position and orientation of the operator's (e.g. surgeon's) head and/or gaze. The tracked position and orientation information may then be used by the processor to update the view or perspective of the virtual reality scene presented to the operator to make the operator feel as if they are immersed in the virtual reality scene. Example position and orientation sensors include, but are not limited to, gyroscopes, accelerometers, structured light tracking systems (e.g. infrared tracking sensors), and any other sensors suitable for tracking position and/or orientation.

In some cases, as shown in FIG. 4, the virtual reality display device 404 may comprise a virtual reality (VR) headset which may also be referred to as VR goggles. As is known to those of skill in the art, a VR headset is a head mounted display (HMD) that is configured to provide virtual reality to the wearer. Specifically, a VR headset is a device worn on the head that has one or more monitors in front of the eyes of the wearer that display images that replace the user's natural environment with a first person view (FPV) of a virtual reality environment. VR headsets typically comprise sensors, such as those described above, to track the position, orientation and/or gaze of the user so that the view or perspective of the virtual reality environment can be automatically updated as the user moves to give the user the impression that they are moving within the virtual reality environment as described above. The VR headset may be any suitable virtual reality headset, such as, but not limited to, the Oculus Rift®, the HTC Vive®, the PlayStation® VR or the Samsung® Gear VR.

While the virtual reality display device is described above as being configured to receive the video stream of the surgical site and generate a virtual reality scene or virtual reality environment based thereon, in other examples, another device may be configured to receive the video stream of the surgical site and generate a virtual reality scene based thereon and provide the generated scene to the virtual reality display device. In these examples, the virtual reality display device may be configured to merely present an appropriate view of the virtual reality scene to the operator.

Figure 5:
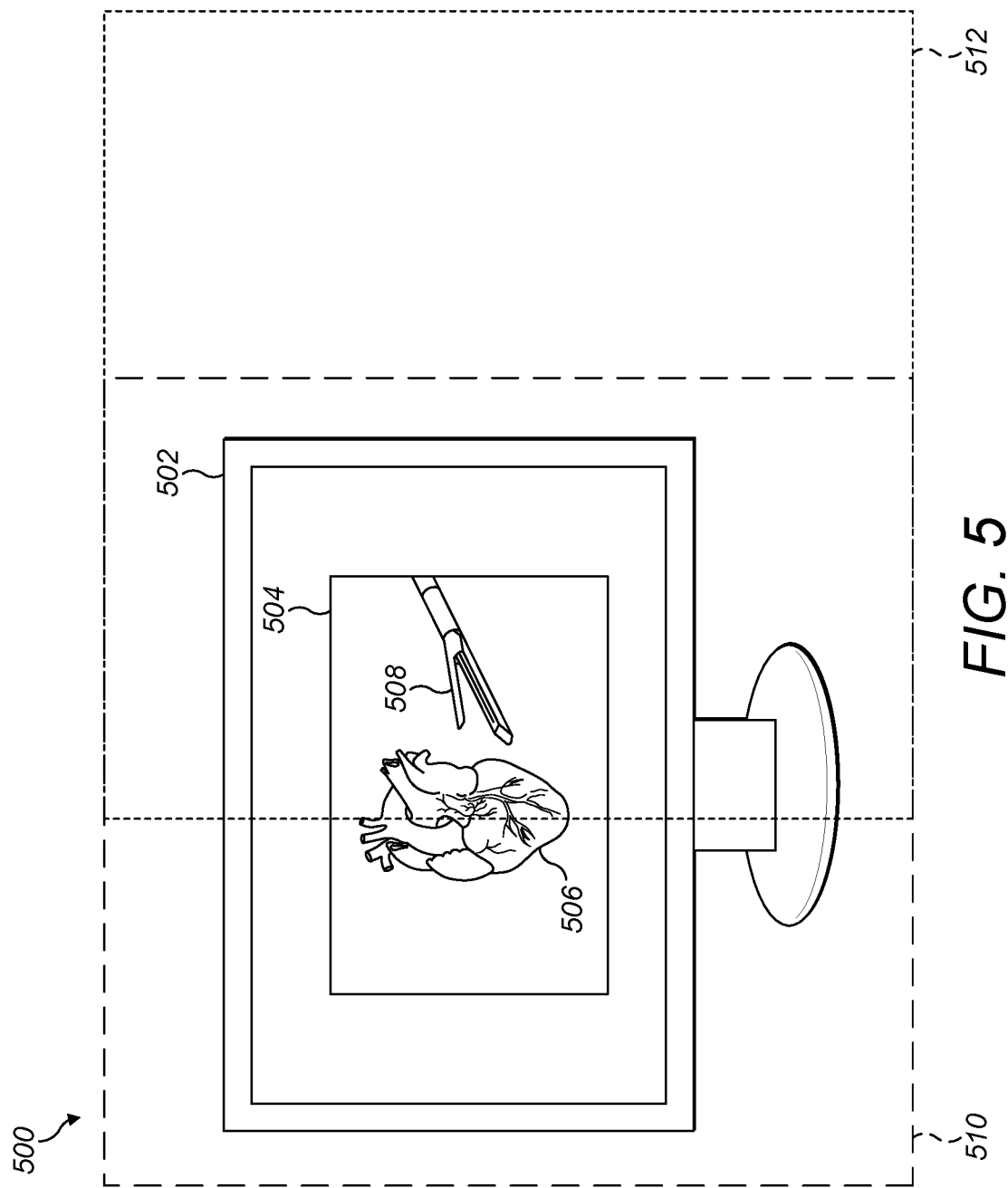
FIG. 5 is a schematic diagram of a first example virtual reality scene which may be generated by the system of FIG. 4.

Reference is now made to FIG. 5 which illustrates an example virtual reality scene 500 which may be generated by the virtual reality display device 404 of FIG. 4. As described above, the virtual reality scene 500 comprises a virtual screen 502 on which a representation 504 of the video stream 410 of the surgical site 412 is displayed. The video stream 410 of the surgical site 412 may comprise images of the anatomy 506 of the patient. The video stream 410 of the surgical site 412 may also comprise images of the instrument end effector 508 attached to, and being controlled by, the surgical robot 402. The virtual screen 502 may be stationary in the virtual reality scene so that when the operator's head is positioned in a first position the operator may be presented with a first view 510 of the virtual reality scene 500 in which the operator can see all of the virtual screen 502, and when the operator moves their head to a second position the operator may be presented with a second view 512 of the virtual reality scene 500 in which the operator can only see a portion of the virtual screen 502. However, as shown in FIG. 5, the field of view of the surgical site that is shown in the virtual screen is the same in both views 510, 512, only the view of the virtual screen is changed. It will be evident to a person of skill in the art that this is only an example of information that may be displayed on the virtual screen 502 in the virtual reality scene presented to the user, and the virtual screen 502 may be used to display additional and/or different information. For example, in addition to displaying a representation of the video stream of the surgical site, the virtual screen 502 may also be used to display, but is not limited to displaying, information relating to the status of the instruments (e.g. such as the energy status of any electrosurgical instruments), surgical robot arms, and/or the hand controllers; alarms; and/or information that provides assistance to the operator in performing a surgical procedure.

Configuring the virtual reality display device 404 to display a representation of the video stream 410 of the surgical site 412 via a virtual screen does not have the technical problem of mapping the operator's head position and/or movement to the image capture device (e.g. endoscope) position and/or movement that arises when a representation of the video stream of the surgical site is presented to the operator (e.g. surgeon) as an immersive virtual reality scene. Configuring the virtual reality display device 404 to display a representation of the video stream 410 of the surgical site 412 via a virtual screen may also (i) allow other information to be displayed in the virtual reality scene and/or (ii) allow the movement of the operator's head and/or gaze to be used to control other aspects of the system. While in the methods and systems described herein the movement and position of the user's head does not automatically control the position and movement of the image capture device (e.g. a movement of the user's head to the right does not automatically cause the image capture device to be moved so that the field of view of the image capture device is moved to the right), in some cases, the operator may still use their head to aide in controlling the position and/or movement of the image capture device. For example, in some cases, the operator may be able to input a command for movement of the image capture device via movement of their head (e.g. by nodding to the left or right, or tilting their head to one side).

Specifically, where a representation of the video stream 410 of the surgical site 412 is presented to the operator as an immersive virtual reality scene there may not be space in the virtual reality scene to display additional information (or a significant amount of additional information) as any additional information may obstruct the operator's view of the surgical site. However, in the systems and methods described herein, where a representation of the video stream of the surgical site is presented to the operator (e.g. surgeon) via a virtual screen in a virtual reality scene, other information can be displayed in the virtual reality scene without affecting the virtual screen and the representation of the video stream 410 of the surgical site 412 displayed thereon. For example, in addition to the virtual screen, the virtual reality scene generated by the virtual reality display device may comprise other virtual objects, such as but not limited to, a real-time representation of the surgical robot or a real-time representation of the surgical robot and the patient. A real-time representation of the surgical robot may be generated by the processor of the virtual reality display device 404 from a video stream of the surgical robot captured by one or more additional cameras in the operating theatre via known video processing techniques. Alternatively, or in addition, the real-time representation of the surgical robot may be generated from the position and/or movement data captured by the sensors (e.g. torque sensors) of the surgical robot. Similarly, a real-time representation of the patient may be generated from a video stream of the patient captured by one or more additional cameras in the operating theatre; or from position and/or movement data captured from one or more other sensors describing the position and/or movement of the patient.

Furthermore, when the operator's head movements and/or gaze are not used to control the position and/or field of view of the image capture device (e.g. endoscope), the operator's head movements and/or gaze can be used to control other aspects of the virtual reality scene, such as controlling which virtual objects are visible. For example, in some cases, the virtual reality display device may be configured to present a view of the virtual scene in which the virtual screen is visible when the operator's head and/or gaze is in a first position, and when the virtual reality display device detects that the operator (e.g. surgeon) has moved their head and/or changed their gaze in a specific direction (e.g. right) from the first position, a view of the view of the virtual scene in which a different virtual object may be displayed. In some cases, the other virtual object may be, for example, a real-time representation of the surgical robot. In other cases, the other virtual object may be a representation of the patient and the surgical robot. In some cases, the operator (e.g. surgeon) may be able to select between representations. For example, the operator (e.g. surgeon) may be able to select between a representation of just the surgical robot and a representation of the surgical robot and the patient. The operator (e.g. surgeon) may also be able to select or change the view of a representation. For example, the operator may be able to select between a plan view of the representation from a position vertically above the surgical robot and/or patient and a perspective view of the representation. In some cases, the operator (e.g. surgeon) may be able to select a representation by pressing a button or otherwise activating an input on an input device (e.g. hand controller); moving their head or gaze in a different direction (e.g. up/down); performing a predetermined gesture; speaking a predetermined voice command; or selecting the representation via a menu system displayed on the virtual screen or elsewhere in the virtual scene.

In some cases, the virtual reality display device 404 may be configured to display other virtual objects in the virtual reality scene to the operator (e.g. surgeon) in response to detecting that the operator has moved their head or their gaze in different directions with respect to the first position. Examples of other virtual objects which may be in the virtual reality scene include, but are not limited to, representations of other objects in the operating theatre, representations of pre-operative patient images (e.g. x-rays etc.), and a representation of the surgical plan. It will be evident to a person of skill in the art that these are examples only and that the virtual reality display device may be configured to include other virtual objects in the virtual reality scene.

Figure 6:
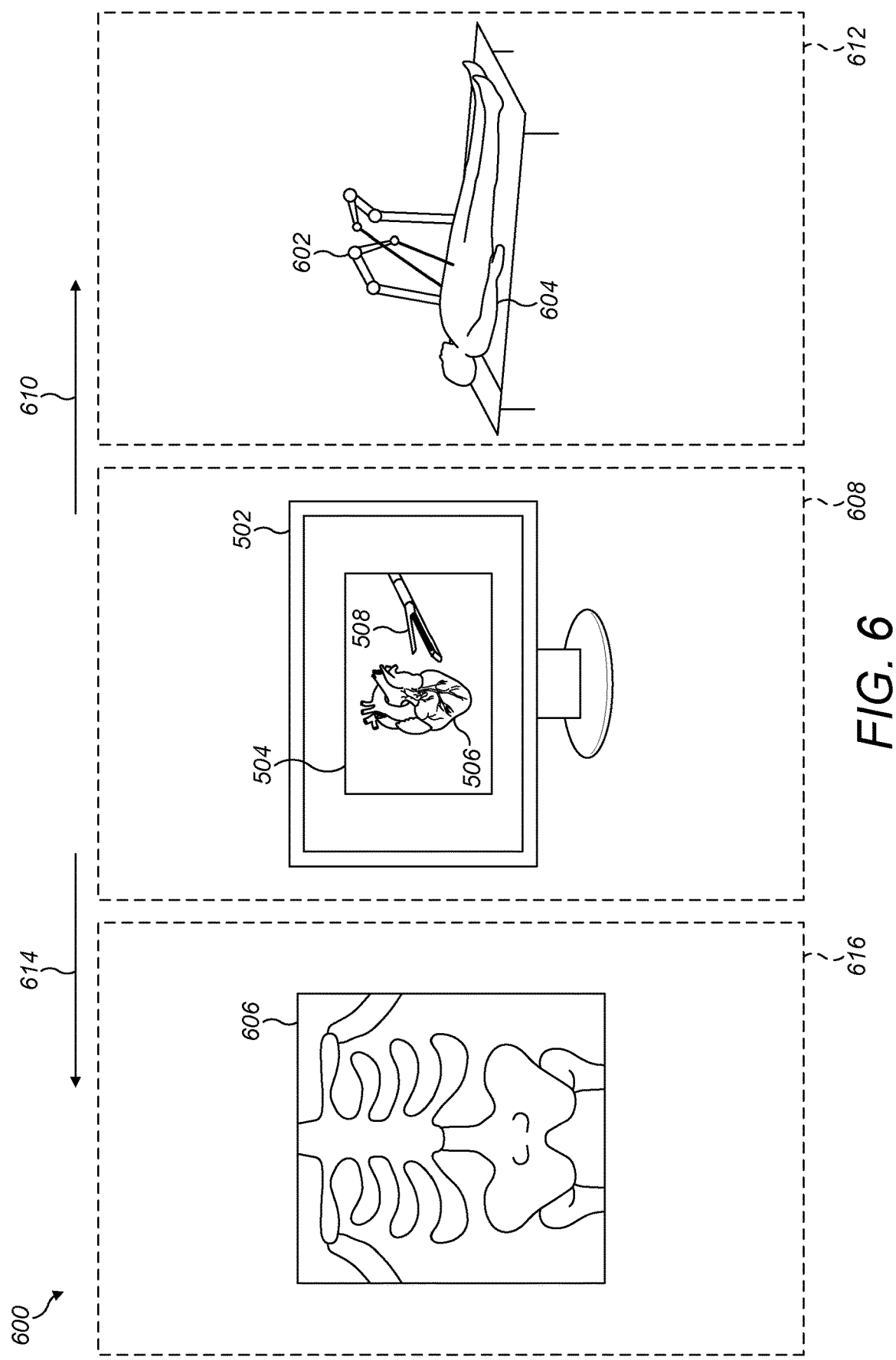
FIG. 6 is a schematic diagram of a second example virtual reality scene which may be generated by the system of FIG. 4.

Reference is now made to FIG. 6 which illustrates a second example virtual reality scene 600 which may be generated by the virtual reality display device 404. The virtual reality scene 600 comprises the virtual screen 502 of FIG. 5 which comprises a representation of the video stream 410 of the surgical site 412 and also comprises a virtual representation 602 of the surgical robot 402 and a virtual representation 604 of the patient 416; and a virtual representation 606 of an x-ray of the patient. It will be evident to a person of skill in the art that these are examples of virtual objects that may be in the virtual reality scene with the virtual screen 502 and that other virtual reality scenes may comprise other and/or additional virtual objects. In this example, when the operator's head is in a first position the virtual reality display device 404 may be configured to present the operator with a view 608 of the virtual reality scene 600 in which the virtual screen 502 is visible. When the operator moves his/her head in a first direction 610 from the first position, the virtual reality display device 404 may be configured to present the operator with a second view 612 of the virtual reality scene 600 in which the virtual representation 602, 604 of the surgical robot and/or patient is/are visible. When the operator moves his/her head in a second direction 614 from the first position, the virtual reality display device 404 may be configured to present the operator with a third view 616 of the virtual reality scene 600 in which the virtual representation 606 of the patient's x-ray is visible. Although in this example the virtual reality display device 404 has been described as being configured to adjust the view of the virtual reality scene presented to the operator in response to detecting movement of the operator's head, in other examples the virtual reality display device 404 may be configured to adjust the view of the virtual reality scene presented to the operator in response to detecting a change in the operator's gaze or in response to detecting a change in the operator's gaze or the operator's head position Returning back to FIG. 4, the input tracking system 406 is configured to track in real-time the position and/or orientation of one or more free-space inputs 418, 420 and provide real-time position tracking and/or orientation information or data 422 to the control unit 408 so that the control unit 408 can control the surgical robot 402 in accordance with the tracked position and/or orientation of the free-space input(s). A free-space input is an input, such as a free hand-held controller, that can be positioned anywhere in free space. In other words, a free-space input is an input in which the position thereof in free space is not constrained. In contrast, an input, such as, a hand controller attached to a linkage assembly is not a free-space input as the position is constrained by the linkage to which the hand controller is attached.

In some cases, the one or more free-space inputs 418, 420 may comprise one or more of the operator's body parts, such as, but not limited to, one or more of the operator's hands and/or fingers. Accordingly, in these cases, the input tracking system 406 may be configured to track, in real time, the position and/or orientation (e.g. in 3D) of one or more of the operator's body parts. The input tracking system 406 may be able to track the position and/or orientation of one or more of the operator's body parts using any suitable method and/or system, such as, but not limited to, an optical tracking system or an inertial tracking system. Where the one or more free-space inputs comprise one or more of the operator's body parts, the operator may be able to enable and disable the use of the tracked position and/or orientation information to control the surgical robot 402 using any suitable means. For example, the operator may be able to enable and disable the use of the tracked position and/or orientation information to control the surgical robot by performing a predetermined gesture or set of gestures with the tracked body part (e.g. hand(s) and/or finger(s)).

As is known to those of skill in the art, an optical tracking system is configured to capture images of the body part (e.g. from image sensors such as a camera) and determine the position and/or orientation from the captured images. In some cases, the body part may be equipped with one are more markers and the position of the body part is determined from the position of the marker(s) in the image. The markers may, for example, be made of a retroreflective material to reflect light that is generated by or near the image sensor and/or they may comprise one or more light generating devices (e.g. one or more LEDs or infrared (IR) emitters). In other cases, the body part may not be equipped with any markers and the optical system may be configured to track the position of the relevant body part(s) from the images alone using special software that is configured to identify the relevant body parts in the images. In contrast, in an inertial tracking system the relevant body part(s) is/are equipped with one or more motion sensors, such as, but not limited to, a gyroscope, magnetometer or accelerometer, which capture motion data that describes the motion of the relevant body part. The captured motion data is provided to a computing device which determines the position and orientation of the body part from the motion data. It will be evident to a person of skill in the art that these are examples only of position tracking systems and that any suitable position tracking system may be used to implement the input tracking system 406.

In other cases, as shown in FIG. 4, the one or more free-space inputs 418, 420 may comprise one or more input devices which may be manipulated by the operator. Input devices which may be used to control a surgical robot include, but are not limited to, hand controllers. In some cases, there may be one hand controller for each hand of the operator. Accordingly, in these cases the tracking system may be configured to track the position of one or more input devices (e.g. hand controllers). The input tracking system 406 may be configured to track the position of an input device using any suitable method or system. For example, the input tracking system 406 may be configured to track the position of an input device (e.g. hand controller) using an optical tracking system or an inertial tracking system described above. In these cases, however, it would be the input device that would be equipped with any markers and/or position sensors.

In some cases, the free-space input devices 418, 420 (e.g. hand controllers) may comprise additional inputs which allow the operator to provide additional information to the control unit 408. For example, in some cases, one or more of the input devices may also comprise one or more buttons, or other inputs, which allow the operator to activate/deactivate the use of the tracked position and/or orientation of the input device (e.g. hand controller) for controlling the robot arm. It will be evident to a person of skill in the art that this is an example only of information that may be provided to the control unit 408 via an input device.

Figure 7:
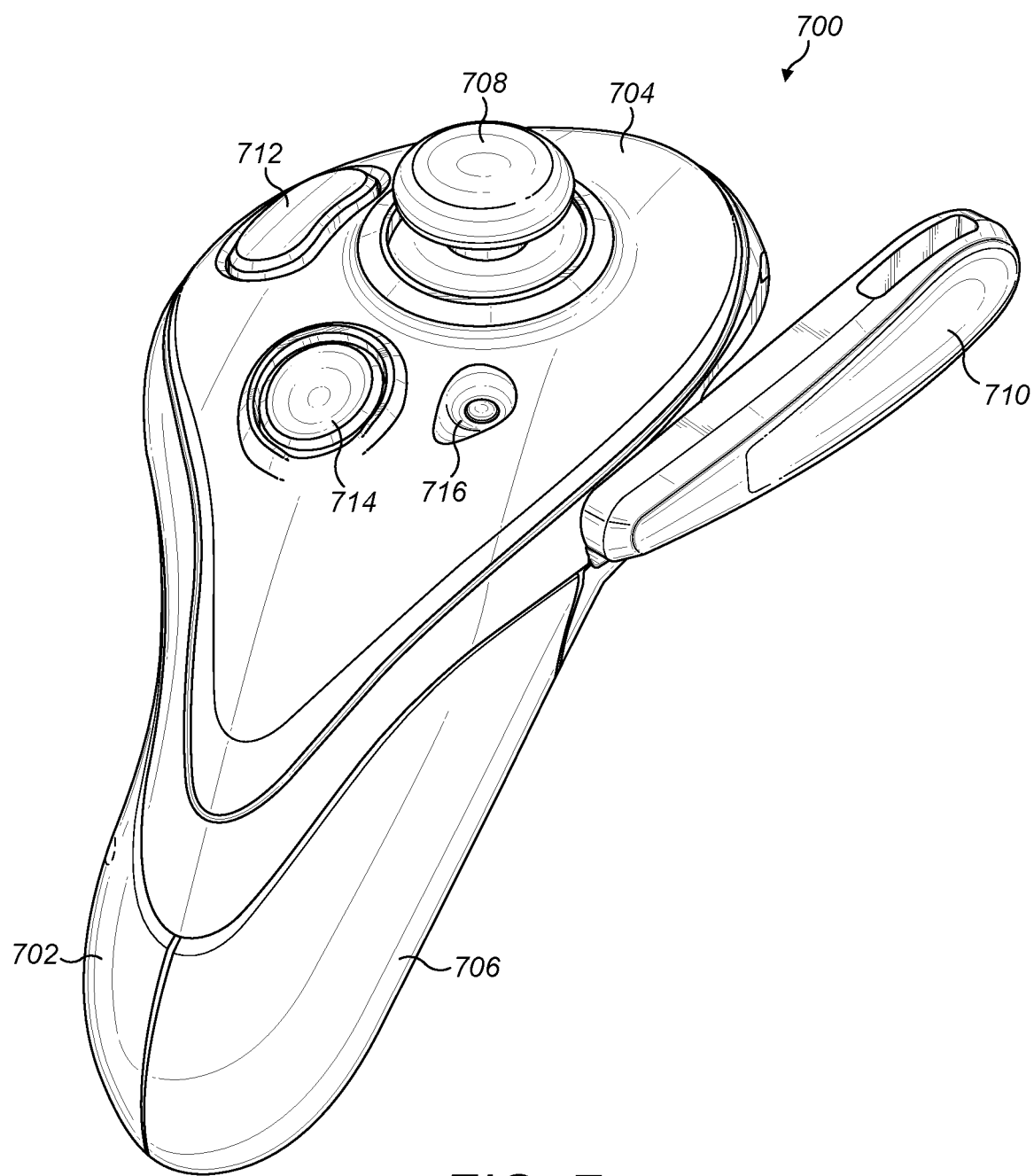
FIG. 7 is a schematic diagram of an example hand controller which may be used in the system of FIG. 4.

An example hand controller 700 which may be used as a free-space input device 418, 420 of the system 400 of FIG. 4 is shown in FIG. 7. The example hand controller 700 of FIG. 7 is intended to be grasped in the operator's right hand. A mirror image hand controller could be used in the operator's left hand. The hand controller 700 comprises a body 702 comprising a head 704 and a grip 706. The grip 706 is configured to sit in the palm of the operator's hand. In this example the position and/or orientation of the body 702 of the hand controller 700 is tracked by the input tracking system 406. In some cases, the position and/or orientation of the body 702 may be tracked by the input tracking system 406 using an optical system as described above. In other cases, the body 702 may be equipped with one or more movement sensors such as an accelerometer or a gyroscope and the input tracking system 406 may be configured to determine and track the position and/or orientation of the hand controller 700 based on the information received from the sensors.

The example hand controller 700 of FIG. 7 also comprises a plurality of inputs 708, 710, 712, and 714 which allow the operator to provide additional information to the control unit 408 to control the surgical robot. In this example, the first input 708 is in the form of a thumbstick that pivots on a base in one or more directions and its position relative to a centre position may be provided to the control unit 408, the second input 710 is in the form of a lever that pivots about the body 702 about an axis (not shown), and the third and fourth inputs 712 and 714 are in the form of buttons. It is evident to a person of skill in the art that this is an example only and that the inputs may take any suitable form; and/or there may be a different number of inputs.

The first input 708 is positioned so that it can be controlled by the thumb of the operator when the hand controller is grasped in the operator's hand. Where the surgical robot has multiple arms the first input 708 may allow the operator to control the position and/or field of view of an image capture device (e.g. endoscope) attached to, and controlled by, another robot arm. This allows the operator to control an instrument attached to one surgical robot arm by moving the body of the hand controller and simultaneously or concurrently control the position and/or field of view of an image capture device (e.g. endoscope) attached to another robot arm by moving the first input 708 left, right, front and/or back relative to the body of the hand controller. In some cases, the first input 708 may only be used to control the movement of an image capture device attached to a robot arm when the operator has engaged the input 708. For example, the input 708 may have a sensor (e.g. capacitive sensor) that detects when the operator has engaged the input 708 and when the sensor detects that the operator has engaged the input 708 then the input 708 may be used to control the position and/or field of view of the image capture device. In some cases, the head 704 may comprise a position sensor to sense the position of the input 708 relative to the body 702. In other cases, the hand controller 700 may comprise a force and/or torque sensor for detecting the force applied to the input 708. In some cases, in addition to being able to move the input 708 left, right, front and/or back relative to the body of the hand controller 700, the operator may be able to push the input 708 down. In these cases, the operator may be able indicate a selection (e.g. on a menu displayed on the virtual screen) by pushing the input 708 down. The operation of the first input 708 and the benefit thereof is described in the Applicant's co-pending UK Patent Application No. 1802992.6 which is herein incorporated by reference in its entirety.

The second input 710 is positioned on the hand controller 700 so as to be controlled by a finger (e.g. pointer or index finger) of the operator when the hand controller is grasped in the operator's hand. The second input 710 may be used by the operator to cause an end effector attached to the corresponding robot arm to perform a pinching or grasping action. For example, the operator may indicate that a grasper instrument (which may also be referred to as a pincer instrument) is to be closed when the operator moves the input 710 toward the body of the hand controller 700 and opened when the operator moves the input 710 away from the body of the hand controller 700. The operation of the second input 710 and the benefit thereof is described in the Applicant's co-pending UK Patent Application No. 1616086.3 which is herein incorporated by reference in its entirety.

The third input 712 is positioned on the hand controller 700 so as to be controlled by the thumb of the operator when the hand controller 700 is grasped in the operator's hand. In some cases, the third input 712 may be referred to as the clutch as it may be used to engage and disengage the hand controller from a robot arm. When the hand controller is engaged with a robot arm the hand controller can be used to control the movement and position of that robot arm and any instrument attached thereto. In contrast, when the hand controller is not engaged (i.e. disengaged) with the robot arm the hand controller cannot be used to control the movement and position of the robot arm and any instrument attached thereto. In other words, when the hand controller is engaged with a robot arm the movement and position of the hand controller controls the movement and position of the robot arm, and when the hand controller is disengaged the movement and position of the hand controller(s) does not affect the movement and position of the robot arm. The operator may disengage the hand controller from the robot arm when, for example, the operator wants to take a break. In some cases, the operator may switch between engaged mode and disengaged mode and vice versa by pressing the third input 712.

The fourth input 714 is positioned on the hand controller 700 so as to be controlled by the thumb of the operator when the hand controller 700 is grasped in the operator's hand. In some cases, the fourth input 714 may be used to activate (e.g. provide electrical energy to) an electrosurgical instrument attached to a selected robot arm (e.g. the electrosurgical instrument attached to the robot arm currently being controlled by the hand controller) with a selected waveform (e.g. CUT waveform or COAG waveform). As is known to those of skill in the art, an electrosurgical instrument is a surgical instrument adapted to perform electrosurgery. Electrosurgery is the passing of a high frequency (i.e. radio frequency) current through tissue to cause a desired effect (e.g. cutting the tissue or coagulating the tissue). Electrosurgical instruments receive the driving current (which may be referred to as a driving electrosurgical signal) from an electrosurgical generator which may also be referred to as an electrosurgery generator, electrosurgical end unit, electrosurgery end unit, or ESU. Electrosurgical generators can typically be configured to generate multiple different current waveforms to achieve different surgical effects. For example, many standard electrosurgical generators can be configured to generate COAG and CUT waveforms. The COAG waveform consists of bursts of radio frequency, which when used at a low power setting causes a desiccation effect, and when used at a high-power setting causes a fulguration effect. The CUT waveform is a continuous waveform at lower voltage, but higher current than COAG, which causes the tissue to be cut.

The example hand controller 700 of FIG. 7 also comprises an indicator 716, specifically an LED indicator, that indicates the current electrosurgical mode of an electrosurgical instrument attached to the selected robot arm. For example, the indicator 716 may emit yellow light when the electrosurgical instrument is active in CUT mode and the indicator 716 may emit blue light when the electrosurgical instrument is active in COAG mode.

Returning to FIG. 4, the input tracking system 406 may comprise one or more processors 424 and a memory 426. The memory 426 stores, in a non-transient way, software code that can be executed by the one or more processors 424 to track the position and/or orientation of one or more free-space inputs (e.g. free-space input devices 418, 420) using any suitable method (such as those described above), generate real-time position and/or orientation data 422 for the one or more free-space inputs (e.g. free-space input devices 418, 420) and provide the real-time position and/or orientation data 422 to the control unit 408.

The control unit 408 is configured to receive data 422 from the input tracking system 406 that indicates the position and/or orientation of the one or more inputs (e.g. hand controllers). The control unit 408 also receives inputs 428 from the surgical robot 402. These inputs 428 may include sensor data from the position sensors and torque sensors located on the robot arm joint. The control unit 408 may receive other inputs from the surgical robot, such as force feedback and/or data from or about the surgical instruments. The control unit 408 drives the surgical robot 402 in response to the inputs it receives from the surgical robot 402 and the input tracking system 406. In some cases, the control unit 408 is configured to convert the movement of the one or more inputs (e.g. hand controllers) into control signals 430 to move the arm joints and/or instrument end effector of the surgical robot 402 in the same way. For example, the control unit 408 may be configured so the end effector of the instrument attached to the arm follows the movement of the corresponding input (e.g. hand controller).

In some cases, to generate the control signals to move the arm joint and/or instrument end effector the control unit 408 generates (or is configured with) a mapping between the orientation and position of the instrument end effector as shown in the video stream of the surgical site and the orientation and position of the input (e.g. hand controller) used to control that instrument that can be used to translate the movement of the input (e.g. hand controller) into a corresponding movement as seen in the video stream of the surgical site. For example, the mapping is generated so that when the operator (e.g. surgeon) moves the input (e.g. hand controller) to the right then the operator (e.g. surgeon) will see in the video stream of the surgical site the end effector move to the right. This allows the operator (e.g. surgeon) to move the input (e.g. hand controller) in a very intuitive way to control the position and movement of the end effector. The control unit 408 may then be configured to convert the movement of an input (e.g. hand controller) into control signals to move the arm joint and/or instrument end effector attached to a robot arm by converting the input's position and orientation in an input Cartesian coordinate reference system to a position and orientation of the instrument end effector in a camera Cartesian coordinate reference system according to the mapping. The control unit 408 may then generate control signals 430 to cause the end effector to be moved so as to have the position and orientation in the camera coordinate reference. In these cases, the mapping between the end effector and the input (e.g. hand controller) may be updated when the field of view and/or the position of the image capture device (e.g. endoscope) is adjusted. An example of the mapping is described in the Applicant's co-pending UK Patent Application No. 1802992.6 which is herein incorporated by reference in its entirety.

Physical operator consoles, such as the physical operator console 200, of FIG. 2, that have input devices attached to linkages and/or gimbals or other fixed structures may be configured so that the linkages and/or gimbals may be driven to provide force feedback to the operator during use to indicate or replicate the forces exerted on the corresponding end effector. This may allow the operator (e.g. surgeon) to be notified of the forces exerted on any end effector being controlled by the operator. However, where, as in the examples described herein, the inputs are free-space inputs, force feedback cannot be provided in this manner. However, instead of providing force feedback, in some cases, the control unit 408 may be configured to provide haptic feedback to the operator in response to detecting from the input 428 received from the surgical robot that a force has been exerted on a corresponding instrument end effector. The existence of the haptic feedback may indicate to the operator that a force has been exerted on the instrument end effector currently being controlled by the operator. The control unit 408 may be configured to adjust a parameter (e.g. frequency, strength) of the haptic feedback to indicate the relative strength of the force. For example, in some cases the haptic feedback may be in the form of vibrations. In these cases, the frequency or strength of the vibrations provided to the operator may be altered to indicate the strength of the force.

Where the one or more inputs are input devices (e.g. hand controllers) the haptic feedback may be provided via the input device (e.g. hand controllers). For example, in some cases, the control unit 408 may be configured to, in response to detecting that a force has been exerted on the instrument end effector currently being controlled by a particular input device (e.g. hand controller), cause that input device to vibrate. Specifically, in these cases the input device may comprise a vibration device that when activated causes the input device (e.g. hand controller) to vibrate. Example vibration devices include, but are not limited to, an eccentric rotating actuator (ERM), a linear resonant actuator (LRS) or a piezoelectric actuator.

Where the one or more inputs are one or more of the operator's body parts the operator may be equipped with a device that can, upon activation by the control unit 408, provide haptic feedback to the operator. For example, in these cases, even though it is the operator's body parts that are tracked the operator may be configured to hold a device (such as a hand controller) that can provide haptic feedback; or the operator may be fitted with a wearable device that can provide haptic feedback.

The control unit 408 may comprise one or more processors 432 and a memory 434.

The memory 434 stores, in a non-transient way, software code that can be executed by the one or more processors 432 to control the surgical robot based on the position and/or orientation information/data 422 received from the input tracking system 406. In some cases, the software code may also be configured to detect from the input 428 received from the surgical robot when a force has been exerted on an instrument end effector currently being controlled by the operator, and, in response to detecting that a force has been exerted on an instrument end effector currently being controlled by the operator, provide haptic feedback to the operator.

While the system 400 of FIG. 4 is shown and described above as being used to control a single surgical robot 402 with a single robot arm, it will be evident to a person of skill in the art that the methods and systems described herein can also be used to control surgical robot systems that comprise a plurality of surgical robots, each with at least one robot arm; or surgical robots with a plurality of robot arms. Specifically, many surgical procedures require the use of multiple surgical robot arms. For example, in many surgical procedures an endoscope is attached to, and controlled by, one robot arm and one or more other end effectors (e.g. surgical instruments such as, but not limited to a pair of graspers (which may also be referred to as pincers), a scalpel; and/or scissors) are each attached to, and controlled by, a different robot arm. The robot arms may form part of the same surgical robot or they may form part of different surgical robots. Where the system 400 of FIG. 4 is used to control multiple robot arms the system 400 may comprise suitable means for determining which robot arm is to be controlled at any time and by which input. For example, in some cases, the operator (e.g. surgeon) may be able to select, using, for example, the inputs and/or the virtual reality display device which of the robot arms is to be currently controlled by the inputs. For example, in some cases, the virtual reality display device may be configured to display on the virtual screen, in addition to a representation of the video stream of the surgical site, information indicating which robot arm(s) and which instrument(s) are currently being controlled and the operator may be able to change the robot arm(s) and instrument(s) currently being controlled by activating one or more inputs (e.g. buttons) on the hand controller.

In some cases, the operator (e.g. surgeon) may be able to control multiple robot arms (and multiple end effectors) at the same time. For example, where there are multiple operator inputs (e.g. multiple hand controllers) the operator (e.g. surgeon) may be able to select which of the inputs (e.g. hand controllers) is to be used to control which of the robot arms (and thus end effectors). For example, where there are two hand controllers the operator may specify that the left hand controller (i.e. the hand controller in the operator's left hand) is to be used to control robot arm 1 attached to end effector 1 and the right hand controller (i.e. the hand controller in the operator's right hand) is to be used to control robot arm 2 attached to end effector 2.

In some cases, an image capture device (e.g. endoscope) may be controlled in a different manner than other end effectors. For example, as described in UK Patent Application No. 1802992.6, in some cases the position and/or orientation of a hand controller may be used to control the position of a surgical instrument attached to a surgical robot arm and another input on the hand controller (e.g. a thumbstick input) may be used to simultaneously control an image capture device (e.g. endoscope) attached to a different surgical robot arm.

Although FIG. 4 shows the control unit 408 and the input tracking system 406 as being separate and distinct devices, in other examples the functions described above as being performed by the control unit 408 and the input tracking system 406 may be performed by a single computing device or a set of related computing devices.

Figure 8:
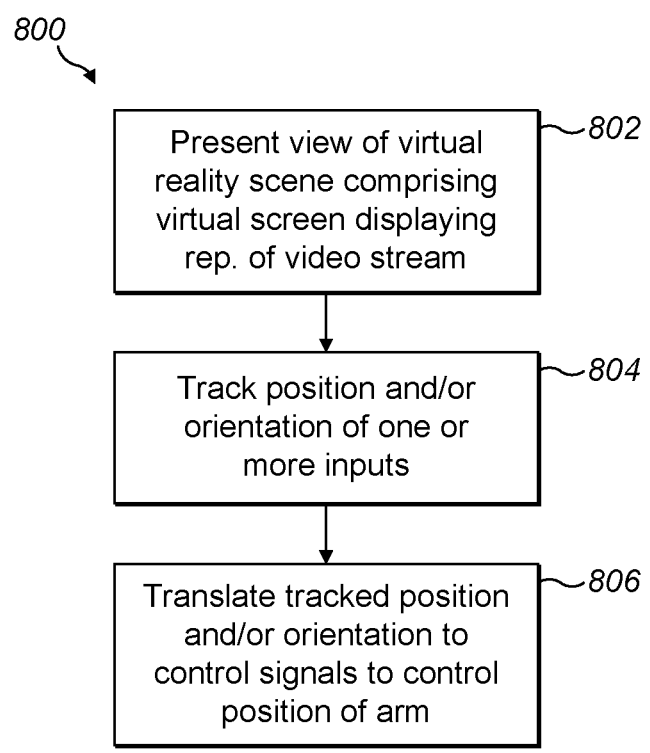
FIG. 8 is a flow diagram of an example method for controlling a surgical robot.

Reference is now made to FIG. 8 which describes a method 800 of controlling a surgical robot using a virtual console which may be performed by the system 400 of FIG. 4. The method 800 begins at block 802 where a virtual reality display device (e.g. the virtual reality display device 404 of FIG. 4) presents a view of a virtual reality scene to an operator of the virtual reality display device. The virtual scene comprises a virtual screen on which a representation of a video stream of a surgical site is displayed. At block 804, an input tracking system (e.g. the input tracking system 406 of FIG. 4) tracks the position and/or orientation of one or more free-space inputs in space. As described above, in some cases, the one or more free-space inputs may comprise one or more of the operator's body parts; and in other cases the one or more free-space inputs may comprise one or more input devices (such as, but not limited to, hand controllers). At block 806, a control unit (e.g. the control unit 408 of FIG. 4) translates the tracked position of the one or more free-space inputs into one or more control signals to control the position of the arm of the surgical robot 806.

In some cases, the method may further comprise receiving the video stream of the surgical site and generating the virtual reality scene therefrom.

Although FIG. 8 illustrates the blocks 802-806 of the method 800 being executed sequentially, in other examples one or more of the steps may be executed concurrently. For example, in some cases block 802 may be executed concurrently with blocks 804 and 806.

Although in the examples described above the virtual screen, on which a representation of the video stream of the surgical site is displayed, is presented to the operator (e.g. surgeon) as part of a virtual reality scene/environment via a virtual reality (VR) display device, in other examples the virtual screen may be presented to the user using other display devices that are capable of presenting a virtual image to a user, such as, but not limited to, a mixed reality (MR) display device or an augmented reality (AR) display device. As is known to those of skill in the art, a VR display device completely replaces the user's real reality (RR) with a computer-generated world so as to trick the user's senses into thinking they are in a different environment or world. Accordingly, a VR display device cuts the user off from the user's RR so that all the user can see is the virtual environment. As described above, examples of VR display devices include, but are not limited to, Oculus Rift®, the HTC Vive®, the PlayStation® VR or the Samsung® Gear VR. In contrast, an AR display device directly or indirectly supplements or augments the real world with computer generated imagery. This may be accomplished, for example, by projecting virtual objects onto an otherwise clear pair of glasses or visor, overlaying them on the real world, or by annotating or projecting virtual objects as overlays on a live view of a scene captured from a camera. An example AR display device includes, but is not limited to, Google Glass®. An MR display device mixes the real world and a virtual world to produce a new environment in which physical and digital objects co-exist. Specifically, a MR display device places virtual objects in the real world as if they were actually there. A user can navigate a mixed reality environment and interact with both real and virtual objects in real time. An example MR display device includes, but is not limited to, Microsoft HoloLens®.

Specifically, in some cases, instead of the virtual screen being presented to the operator (e.g. surgeon) as part of a virtual reality scene/environment via a virtual reality display device (e.g. a virtual reality headset), the virtual screen may be presented to the user as an overlay on, or part of, a real world view of the operating theatre by an AR display device or an MR display device. For example, a piece of material may be placed in the operating room which can be uniquely identified by the AR or MR display device (or the computer generating the virtual screen and the placement thereof in the real world) and then the AR or MR display device maps or aligns the virtual screen in the real world with the piece of material. In this way the virtual screen is anchored in the real world to the location of the piece of material in the same way the virtual screen was anchored in the virtual reality scene in the examples described above. In some cases, the piece of material may have a particular colour (e.g. white) to be identified by the AR or MR display device as the location for the virtual screen. The piece of material may be sized so as to have the desired dimensions of the virtual screen in the real world. In some cases, the piece of material may be rectangular-shaped. Different sized pieces of material may be used for different procedures or in different operating rooms to, for example, accommodate the space in the operating room for a particular procedure or operation. In some cases, the piece of material may be foldable or flexible so that it can be easily moved from one location to another compared to a display screen or monitor of the same size.

Presenting the virtual screen to the operator (e.g. surgeon) using an AR display device or an MR display device, rather than presenting the virtual screen to the operator (e.g. surgeon) as part of an immersive virtual reality scene/environment using a VR display device may alleviate some of the issues with immersing the operator in a virtual reality environment. Specifically, when the operator is immersed in a virtual reality scene/environment the operator is cut-off from the rest of the operating room team. In contrast, presenting the virtual screen to the operator (e.g. surgeon) as part of the real world allows the operator to be able to see the rest of the operating room team during the procedure which provides them with a better overall understanding of what is happening in the operating room.

In yet other cases, the display device may be in the form of a projection device (e.g. a front projection or a rear projection device or projector) that is configured to project the virtual screen on a wall, a projection screen, or a piece of material (which in some cases may be portable). For example, similar to the AR and MR display device cases, there may be a piece of material that may be placed in the operating room and the virtual screen may be projected onto this piece of material. This may allow the virtual screen that is displayed to the user to be larger than a virtual screen displayed via a VR, AR or MR headset, which may allow the virtual screen, and specifically the representation of the real-time video stream of the surgical site, to be displayed at a higher resolution. Like in the AR and MR display device cases, the piece of material may have a particular colour (e.g. white) to be identified by the projection device as the location for the virtual screen. In some cases, the piece of material may be rectangular-shaped. Different sized pieces of material may be used for different procedures or in different operating rooms to, for example, accommodate the space in the operating room for a particular procedure or operation. In some cases, the piece of material may be foldable or flexible so that it can be easily moved from one location to another compared to a display screen or monitor of the same size.

Furthermore, although the example systems described above comprise an input tracking system configured to track the position and/or orientation of one or more free-space inputs, in other examples the input tracking system may be configured to track the position and/or orientation of traditional surgical robot input devices such as those described above with reference to FIG. 2 (e.g. handgrips or hand controllers mounted on parallelogram linkages). Since it is often the display of a physical console which causes the physical console to be bulky and large, many of the problems with physical consoles, such as the physical consoles taking up a lot of space and being difficult to move around, may be alleviated by using a VR, AR or MR display device to present a virtual screen to the user instead of a physical display. Furthermore, using traditional surgical robot input devices (e.g. handgrips or hand controllers mounted on parallelogram linkages) alleviates the issue of not being able to receive force feedback when using free-space inputs which may be seen as a key disadvantage to many surgeons. Accordingly, a system for controlling a surgical robot that comprises: a VR, AR or MR display device for presenting a virtual screen to an operator upon which a representation of the real-time video stream of a surgical site is displayed; and traditional input devices to control the position and/or orientation of the robot arms (and any instruments attached thereto), may have many of the advantages of the completely virtual system described above (e.g. a system comprising a VR, AR or MR display device and free-space inputs) without some of the disadvantages thereof.

The applicant hereby discloses in isolation each individual feature described herein and any combination of two or more such features, to the extent that such features or combinations are capable of being carried out based on the present specification as a whole in the light of the common general knowledge of a person skilled in the art, irrespective of whether such features or combinations of features solve any problems disclosed herein. In view of the foregoing description it will be evident to a person skilled in the art that various modifications may be made within the scope of the invention.

The invention claimed is:

1. A system for controlling a surgical robot, the surgical robot comprising a base, and an arm extending from the base to an attachment for an instrument, the arm comprising a plurality of joints whereby a configuration of the arm can be altered, the system comprising:
a head mounted display device configured to present a virtual screen to an operator of the head mounted display device, the virtual screen being stationary in a scene visible to the operator, wherein a representation of a real-time video stream of a real world surgical site captured by an image capture device is displayed on the virtual screen, wherein the head mounted display device comprises a virtual reality headset configured to present a view of a virtual reality scene to the operator of the virtual reality headset, the virtual reality scene comprising the virtual screen;
an input tracking system configured to track a position and/or orientation of one or more free-space inputs; and
a control unit configured to translate the tracked position and/or orientation of the one or more free-space inputs into one or more control signals which control a position of the arm of the surgical robot.

2. The system of claim 1, wherein the virtual reality headset comprises one or more sensors configured to track a position of the operator's head and/or the operator's gaze when the operator is using the virtual reality headset, and the virtual reality headset is further configured to present a different view of the virtual reality scene to the operator in response to detecting from the one or more sensors a change in position of the operator's head and/or a change in the operator's gaze.

3. The system of claim 2, wherein the virtual reality headset is configured to, in response to detecting that the operator's head and/or the operator's gaze is in a first position, presenting a view of the virtual reality scene in which the virtual screen is visible.

4. The system of claim 3, wherein the virtual reality headset is configured to, in response to detecting that the operator's head and/or the operator's gaze has moved in a first direction with respect to the first position, presenting a view of the virtual reality scene in which another virtual object is displayed.

5. The system of claim 4, wherein the other virtual object is a real-time representation of the surgical robot.

6. The system of claim 4, wherein the other virtual object is a real-time representation of the surgical robot and a patient.

7. The system of claim 4, wherein the other virtual object is a representation of one or more patient pre-operative scans.

8. The system of claim 4, wherein the virtual reality headset is configured to, in response to detecting that the operator's head and/or the operator's gaze has moved in a second direction with respect to the first position, present a view of the virtual reality scene in which a further virtual object is displayed.

9. The system of claim 1, wherein a field of view of the surgical site shown in the video stream is not automatically controlled by movement of the operator's head or the operator's gaze.

10. The system of claim 1, wherein the one or more free-space inputs comprises a hand controller.

11. The system of claim 1, wherein the control unit is further configured to, in response to detecting that the arm of the surgical robot or an instrument attached thereto has had a force exerted thereon, cause feedback indicative of the exerted force to be provided to the operator.

12. The system of claim 11, wherein the control unit is further configured to adjust a parameter of the feedback based on a magnitude of the detected force.

13. The system of claim 1, wherein the video stream of the surgical site is captured by an endoscope attached to an arm of the surgical robot and the position of the endoscope is controlled by the surgical robot.

14. The system of claim 1, wherein the head mounted display device is further configured to receive the video stream of the surgical site and generate the virtual screen from the video stream of the surgical site.

15. The system of claim 1, further comprising the surgical robot.

16. The system of claim 1, wherein:
the control unit is further configured to receive operator input from at least one of the one or more free space inputs indicating a desired position and/or field of view of the image capture device and control the position and/or field of view of the image capture device in dependence on the received operator input.

17. A method of controlling a surgical robot, the surgical robot comprising a base, and an arm extending from the base to an attachment for an instrument, the arm comprising a plurality of joints whereby a configuration of the arm can be altered, the method comprising:
  presenting, using a head mounted display device, a virtual screen on which a representation of a video stream of a real world surgical site captured by an image capture device is displayed, the virtual screen being stationary in a scene visible to an operator of the head mounted display device, wherein the head mounted display device comprises a virtual reality headset configured to present a view of a virtual reality scene to the operator of the virtual reality headset, the virtual reality scene comprising the virtual screen;
  tracking, using an input tracking system, a position in space of one or more free-space inputs; and
  translating the tracked position of the one or more free-space inputs into one or more control signals to control a position of the arm of the surgical robot.

* * * * *